US007736508B2

(12) United States Patent
Limcaco (10) Patent No.: US 7,736,508 B2
(45) Date of Patent: Jun. 15, 2010

(54) SYSTEM AND METHOD FOR BIOLOGICAL WASTEWATER TREATMENT AND FOR USING THE BYPRODUCT THEREOF

(75) Inventor: Christopher A. Limcaco, 3632 Chancellor Dr., Greenwood, IN (US) 46143

(73) Assignee: Christopher A. Limcaco, Greenwood, IN (US)

(*) Notice: Subject to any disclaimer, the term of this patent is extended or adjusted under 35 U.S.C. 154(b) by 156 days.

(21) Appl. No.: 11/957,648

(22) Filed: Dec. 17, 2007

(65) Prior Publication Data

US 2008/0135475 A1 Jun. 12, 2008

Related U.S. Application Data

(63) Continuation-in-part of application No. 11/856,175, filed on Sep. 17, 2007.

(60) Provisional application No. 60/845,490, filed on Sep. 18, 2006.

(51) Int. Cl.
*C02F 3/32* (2006.01)
(52) U.S. Cl. .................................. 210/602; 210/603
(58) Field of Classification Search .................. 210/601, 210/603, 621, 602
See application file for complete search history.

(56) References Cited

U.S. PATENT DOCUMENTS

| 3,598,726 | A | | 8/1971 | Welch | |
|---|---|---|---|---|---|
| 4,240,210 | A | * | 12/1980 | Huang | 34/520 |
| 4,267,038 | A | * | 5/1981 | Thompson | 210/602 |
| 4,289,625 | A | * | 9/1981 | Tarman et al. | 210/603 |
| 4,344,847 | A | * | 8/1982 | Grenet | 203/11 |
| 4,971,690 | A | | 11/1990 | Justice | |

(Continued)

FOREIGN PATENT DOCUMENTS

WO 95/24548 A1 9/1995

(Continued)

OTHER PUBLICATIONS

Ann C. Wilkie and Walter W. Mulbry, Recovery of Dairy Manure Nutrients by Benthic Freshwater Algae, Bioresource Technology 84 (2002) 81-91.

(Continued)

*Primary Examiner*—Fred Prince
(74) *Attorney, Agent, or Firm*—Maginot, Moore & Beck, LLP (57) ABSTRACT

A wastewater treatment system and process biologically treats wastewater to produce substantially clean water effluent and byproducts. The treatment system includes an array of media wheels that rotate into and out of exposure to sunlight for sustained algae growth. One byproduct is algae removed from the rotating media wheels, which may be provided to other processing facilities to produce, for instance, bio-diesel fuel. Waste $CO_2$ from the processing facility may also be returned to the treatment system for enhanced algae growth. Bacteria is provided to form a symbiotic relationship with the algae, fueled by sunlight to effectively remove toxic materials from the wastewater. Large scale facilities may integrate the treatment systems in a regenerative cycle in which the biomass obtained from the algal colonies is used in a separate facility and byproducts of the operation of the separate facility are used by the treatment system to fuel further algal growth.

15 Claims, 8 Drawing Sheets

U.S. PATENT DOCUMENTS

| | | | |
|---|---|---|---|
| 5,647,983 | A | 7/1997 | Limcaco |
| 5,755,961 | A | 5/1998 | Limcaco |
| 6,158,386 | A | 12/2000 | Limcaco |
| 6,171,499 | B1 * | 1/2001 | Bouchalat ............ 210/603 |
| 6,410,283 | B1 * | 6/2002 | Rehmat et al. ........ 435/167 |
| 6,416,993 | B1 | 7/2002 | Wexler et al. |
| 6,477,841 | B1 | 11/2002 | Yantovsky |
| 6,569,332 | B2 * | 5/2003 | Ainsworth et al. ..... 210/603 |
| 6,824,682 | B2 * | 11/2004 | Branson .............. 210/603 |
| 2004/0256297 | A1 | 12/2004 | Jowett |
| 2005/0269259 | A1 * | 12/2005 | Dunlop et al. ........ 210/602 |

FOREIGN PATENT DOCUMENTS

WO 9524548 9/1995

OTHER PUBLICATIONS

Walter W. Mulbry and Ann C. Wilkie, Growth of Benthic Freshwater Algae on Dairy Manures, Journal of Applied Phycology, 13: 301-306, 2001.

Coghlan, Andy, "Technology: Algal Power Gives A Clean Burn", New Scientist Print Edition, Jan. 16, 1993, 2 pages.

National Renewable Energy Laboratory, Outdoor Studies and Systems Analysis, p. 145, 1 page.

* cited by examiner

SYSTEM AND METHOD FOR BIOLOGICAL WASTEWATER TREATMENT AND FOR USING THE BYPRODUCT THEREOF

REFERENCE TO RELATED APPLICATION

This application is a continuation-in-part of and claims priority to application Ser. No. 11/856,175, filed on Sep. 17, 2007, pending, which claims priority to provisional patent application No. 60/845,490, filed on Sep. 18, 2006.

BACKGROUND

The present invention relates to wastewater treatment systems and processes, and particularly to ecological and biological treatment systems. More specifically, the invention concerns systems and methods for treating wastewater and for using the byproducts of such treatment.

The present invention addresses two critical environmental needs—efficient treatment of wastewater from a variety of sources and development of "green" and renewable energy sources. Wastewater treatment has grown significantly from its origins for treatment of metropolitan sewage. Environmental protection regulations promulgated in the 1900's require treatment of effluent from industrial concerns prior to drainage into a common waterway. Typically, wastewater treatment involves three stages, called primary, secondary and tertiary treatment. First, the solids are separated from the wastewater stream, initially by screens and coarse filters, and then typically by sedimentation or settling within a pre-treatment containment. The separated solids can be removed by skimming (for floating solids) and by sludge scrapers for settled solids.

In the secondary stage, dissolved biological matter is progressively converted into a solid mass by using indigenous, water-borne bacteria. Secondary treatment systems are generally classified as either fixed film or suspended growth. Fixed-film treatment process including trickling filters and rotating biological contactors where the biomass grows on media and the sewage passes over its surface. In suspended growth systems—such as activated sludge—the biomass is well mixed with the sewage and can be operated in a smaller space than fixed-film systems that treat the same amount of water. However, fixed-film systems are more able to cope with drastic changes in the amount of biological material and can provide higher removal rates for organic material and suspended solids than suspended growth systems.

Rotating biological contactors (RBCs) are mechanical secondary treatment systems, which are robust and capable of withstanding surges in organic load. RBCs include rotating disks that support the growth of bacteria and micro-organisms present in the sewage, which breakdown and stabilise organic pollutants. Oxygen is obtained from the atmosphere as the disks rotate. As the micro-organisms grow, they build up on the media until they are sloughed off due to shear forces provided by the rotating discs in the sewage. Effluent from the RBC is then passed through final clarifiers where the micro-organisms in suspension settle as a sludge. The sludge is withdrawn from the clarifier for further treatment In the tertiary, or final, stage, the biological solids are neutralized for disposal or re-use, and the treated water may be disinfected chemically or physically (for example by lagoons and micro-filtration). The final effluent can be discharged into a stream, river, bay, lagoon or wetland, or it can be used for the irrigation of a golf course, green way or park. If it is sufficiently clean, it can also be used for groundwater recharge. A typical tertiary system may include carbon filters to remove certain toxins, and clarifiers configured to remove other constituents, such as nitrogen and phosphorus. In larger systems, the tertiary stage may incorporate lagooning or discharge into wetlands of engineered reedbeds.

The secondary stage of wastewater treatment is notoriously problematic due to the complexity of maintaining large bacterial colonies necessary to biologically treat the wastewater. Maintaining larger and more complex bacterial colonies has unfortunately manifested itself in more costly and complicated equipment and facilities, with a commensurate increase in mechanical failure and equipment downtime. Another potential problem is that the bacterial colonies are intended to convert the wastewater contaminants into other presumably less toxic forms, such as methane, nitric oxide and $CO_2$ gases. Each of these byproducts of bacterial activity is considered to be a greenhouse gas and a contributor in some measure to global warming.

In the 1950s, wastewater treatment strategies were developed that capitalized on the symbiotic relationship between bacteria and algae. Algae produces oxygen necessary for aerobic bacterial growth and bacteria produces $CO_2$ needed for algal growth. The only external input to fuel this symbiotic relationship is sunlight. This strategy was first successfully implemented in open lagoons and wetland treatment facilities. These on-site systems had obvious limitations, such as land space, geography and topography, water clarity, etc. In addition, the on-site systems were prone to algae blooms that would overrun and clog the systems. These limitations led to the development of the algae raceway in the 1970s. The algae raceway is essentially a flume in which nutrient-rich water is allowed to course while exposed to sunlight. The resultant algal biomass is harvested by mechanical means. One significant detriment of the algae raceway is that it requires a large surface area for adequate exposure to sunlight. In addition, the raceway requires a shallow water level to function, which inherently limits the volume and flow of wastewater that can be treated by any particular raceway facility.

The present invention avoids the problems associated with RBCs, open on-site systems and algae raceways.

The second critical environmental need addressed by the present invention is the need for "green" and renewable energy sources. So-called "green" energy sources cause only minimal detrimental impact on the environment. The optimum "green" energy source would produce a net ecological benefit by, for instance, reducing pollutants and re-using waste materials to generate energy or provide a clean energy source.

The need for a renewable energy source has become particularly acute and the subject of widespread concern. For example, fossil-fuel based energy (gas and oil) are known to be finite. While the debate rages as to exactly how finite is "finite", much evidence suggests that worldwide oil production will peak in around 2010. When the wells will run dry is also hotly debated, but some analysts have suggested that the oil supply will end as early as 2035, while more conservative estimates move the date out to 2060. Nevertheless, there is no question that the fossil fuels will be depleted.

Awareness of the limited life of fossil fuels has prompted significant research and development for renewable energy sources. Much research has been devoted to alternative energy sources, such as solar, wind and wave power. However, these alternative energy sources do not appear to have the near-term capability of satisfying the need for petroleum-type fuels—i.e., gasoline and diesel fuels. Research in the 1980s focused on developing gasoline and diesel fuels based on renewable resources, such as corn-based ethanol and bio-diesel. Most bio-diesels are based on cash crops, such as soybeans, which require a significant amount of energy to grow and harvest. Moreover, the cash crops themselves must be devoted to the production of biodiesel.

Research conducted from 1980-1996 by the U.S. Department of Energy established algae as a source of bio-diesel. Biofuel is produced by digestion for methane or hydrogen fuels, lipid extraction for bio-diesel and distillation for ethanol. Unlike the other forms of bio-diesel fuel, the production of the algae itself is utilitarian—wastewater treatment being a prime example. In addition to its benefits as a precursor to biofuels, algae has been developed for other uses, such as an organic fertilizer in lieu of the more expensive and increasingly scarce nitrogen fertilizers. Collected algae biosolids has even been proposed as a basis for an alternative textile, for high value chemicals such as medicines, and for nutritional additives especially for animal feed.

Biodiesel has been investigated by the U.S. Department of Energy as part of its "Aquatic Species Program" that began in 1978. Funding for this program was eliminated in 1995, but growing concerns over non-renewable fossil fuels has prompted growing interest in this seemingly infinite and renewable source for diesel fuel. The DOE's approach has been to create algae ponds or "raceways" near factories that generate waste $CO_2$. The waste $CO_2$ and other nutrients are injected into water circulating around a racetrack shaped pond. Algae growing in the circulating water feeds on the $CO_2$. The algae is eventually diverted from the pond for further processing as a biofuel. Thus, the DOE focus has been on artificially creating a growing environment for algae by recycling waste $CO_2$ from a factory or a coal-fired power plant. Of course, one significant limitation of this technology is that it is tied to a source of waste $CO_2$. Another detriment is that this proposed technology requires a large raceway pond, and ultimately a large amount of dedicated land in order to support enough algae to accept the waste $CO_2$ and to produce a meaningful amount of algae for use in making a biofuel. Since the algae requires exposure to sunlight for growth, the ponds must be shallow, which means that the surface area of the pond must be very large to support the algae colonies. The large size of the pond also means that the useful "season" may be limited in certain locales and climates due to freezing of the pond.

The present invention capitalizes on this multiple functionality of algae—especially on algae's role as a catalyst for biologically treating wastewater and as a source of biofuel—while eliminating the significant problems associated with prior algae-based waste treatment systems.

SUMMARY OF THE INVENTION

In accordance with one feature of the invention, wastewater treatment system centers around the production of algae bio-solids using a variety of aqueous nutrient sources including but not limited to agricultural, industrial, municipal, and other wastewater sources. These algae bio-solid byproducts are then provided as input for generating hydrogen gas, biofuel, fertilizer, and animal feed additives.

In one embodiment, the input to the system is wastewater containing biological and other waste obtained from a variety of sources. The inventive system contemplates a relatively high volume flow of wastewater into the system, such as might arise in a municipal wastewater treatment plant; however, the principles of the invention are applicable for any volume of wastewater being processes.

In a first step in the process, the raw wastewater is pre-screened to remove undesirable solids, which may be disposed of in a conventional manner, such as delivery to a landfill. In one system, initial screening of solids occurs in a primary treatment tank where the undesirable solids settle to the bottom portion of the tank. The primary treatment tank in this system also preferably incorporates a flow equalization feature to control the flow of pre-screened wastewater to raw sewage pumps.

The pre-screened wastewater then enters a secondary treatment tanks via a timed dose volume, equalized continuous flow, or other engineered method of distributing flow into the treatment tanks. The wastewater entering the secondary treatment tanks may contain an aqueous solution of nutrients which facilitates the growth of bacteria and algae. Thus, in accordance with one aspect of the inventive system and method, this nutrient-laden wastewater passes through aerobic, anaerobic, and anoxic zones that are hospitable to varying species of bacteria able to take advantage of the appropriate environment and available nutrients. The heterogeneous cultures of bacteria perform a variety of biological processes which either assimilate nutrients into a biomass or convert nutrients into less environmentally toxic forms. One biological reaction facilitated by bacteria in the secondary tank is:

$$(CH_2O)_x + O_2 \rightarrow CO_2 + H_2O$$

where $(CH_2O)_x$ represents the organic substances biochemical oxygen demand (BOD) introduced via the wastewater source.

In one embodiment, the secondary treatment tank includes a rotating wheel construction that provides surfaces for colonization by algae. This rotating wheel system facilitates the following biological reaction occurring by photosynthesis:

$$CO_2 + 2H_2O + \text{Solar Energy} \rightarrow (CH_2O)_x + O_2 + H_2O$$

where $(CH_2O)_x$ represents the organic matter fixed in the algal biomass. The inventive system capitalizes on a beneficial symbiosis between algae and bacteria which results in a cost effective method of producing algae. The bacteria rely on the presence of $O_2$ produced by the algae and the algae rely on the $CO_2$ produced by the bacteria. The growth of bacterial and algal colonies in the secondary treatment tank results in a reduction of BOD (biochemical oxygen demand) from the wastewater source, as well as a reduction in suspended solids, nitrogen, phosphorous, and other nutrients in the discharged effluent to readily meet the discharge limitations established by regulatory agencies. Since the algae uses solar energy in its photosynthetic uptake of nutrients; the rotating wheel of the present system is intentionally exposed to sunlight to take advantage of this source of free energy. The net effect is an efficient environment for the production of bacterial and algal bio-solids found in no other system used to treat wastewater.

In certain embodiments, the rotating wheels are rotated individually by injecting air from air pumps beneath each wheel. The use of injected air to drive the rotating wheels eliminates the need for mechanical drive mechanisms which have the potential to fail as biomass accumulates on the surface of the rotating wheel. The rotation speed of the wheels is regulated depending on the depth of water in each wheel compartment. The injected air also serves to add $O_2$ to the aqueous solution which is necessary for biological processes employed by both bacterial and algal communities in the tank to uptake nutrients. Additionally, the turbulence produced by the injected air in the tank causes solids-laden algae to break free and enter the flow of the water passing through the system. Continuous flow through the system carries the free algae particles, as well as any solids collected by the algae, toward the exit point of the system.

Water exiting the secondary treatment tank consequently contains a percentage of algal, bacterial, and inert solids. The bio-solids may be separated from the treated water using a variety of separation techniques, including but not limited to centrifuge and belt filter press. The residual water may then be disinfected and directly discharged to a receiving stream, applied to adjacent land in accordance with regulatory requirements or returned to holding tanks for re-use.

In a further aspect of the present invention, virtually all of the byproducts of this ecological and biological treatment process are used in other processes. For instance, in one aspect, as the algae grows on the rotating wheels an algae colony will eventually reach a "critical mass" where the colony is easily dislodged from the rotating wheel. Removal of this solids-laden algae colony may be accomplished automatically by air and water flow across the growing surface of the wheel. These bio-solids settle at the base of the secondary treatment tank for tertiary treatment, including converting nitrates into nitrogen gas that can be percolated from the water exiting the tank. The remaining bio-solids may be removed for further processing as a biofuel, fertilizer, etc. The amount of biosolids extracted may be calibrated relative to the constantly occurring biological reactions, including nitrogen production. In certain facilities, the settled biosolids may be extracted or removed before any significant tertiary treatment occurs.

The extracted algae-based biosolids are conveyed for further processing, such as conversion into a high density liquid form of energy—natural oil in the form of triacylglycerols or TAGs. It is known that micro algaes can produce up to 60% of their body weight in TAGs, making this plant species a very viable source of biofuel, and particularly biodiesel. Biodiesel is obtained by combining TAG with simple alcohols through transesterification. Biodiesel performs as well as petroleum diesel but with significantly fewer emissions of particulate matter, $CO_2$, hydrocarbons and $SO_x$.

In one larger scale system, the algae-based biosolids are used in a regenerative energy system. Biosolids obtained from a secondary treatment system may be treated and combusted as part of an electricity generation process. The byproducts of the combustion, such as $CO_2$, may be fed back to the treatment tank to enhance and maximize the treatment process as well as the generation of algal colonies. As the process continues, the combustion byproducts recycled back to the treatment system exceed the needs of the system, at which point an additional treatment system may be brought on line. This additional system produces additional biosolids that can be likewise combusted to generate electricity. Further treatment systems may be brought on line as the combustion byproducts are recycled back to the systems until a desired equilibrium point is reached.

DESCRIPTION OF THE ILLUSTRATED EMBODIMENTS

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

In one embodiment, a wastewater treatment facility 10 is provided that is adapted for relatively small-scale usage. For instance, the facility 10 shown in FIG. 1 may be used for treatment of residential or commercial wastewater where the wastewater flow rate is as low as about 500 gal/day. A facility of this type may also be used for moderate wastewater flows up to about 25,000 gal/day. The system 10 includes a primary treatment tank 15, a secondary treatment system 30 and a tertiary treatment tank 50. The primary treatment tank 15 functions to remove large inert solids from the wastewater stream and to provide equalized water flow into the secondary treatment system 30. Thus, the primary tank 15 includes an inlet 16 connected to a source of wastewater, such as the water drain and sewage drains for a residential or commercial facility. The wastewater inlet 16 is at an upper portion of the tank 17. A wall 18 separates the tank into inflow and an outflow portions, 17a and 17b, respectively. A weir opening 19 is defined between the two portions. In a specific embodiment, the weir opening isolates a lower one-third of the volume of the inflow portion 17a as a pre-treatment area for settling of any large inert solids contained in the wastewater stream. The remainder of the inflow portion 17a serves as an equalization volume as the wastewater inflow seeks a common level between the inflow and outflow portions of the tank 17. The primary treatment tank thus acts to store wastewater and to equalize inflow and outflow to reduce hydraulic surges ahead of the secondary system 30.

Figure 1:
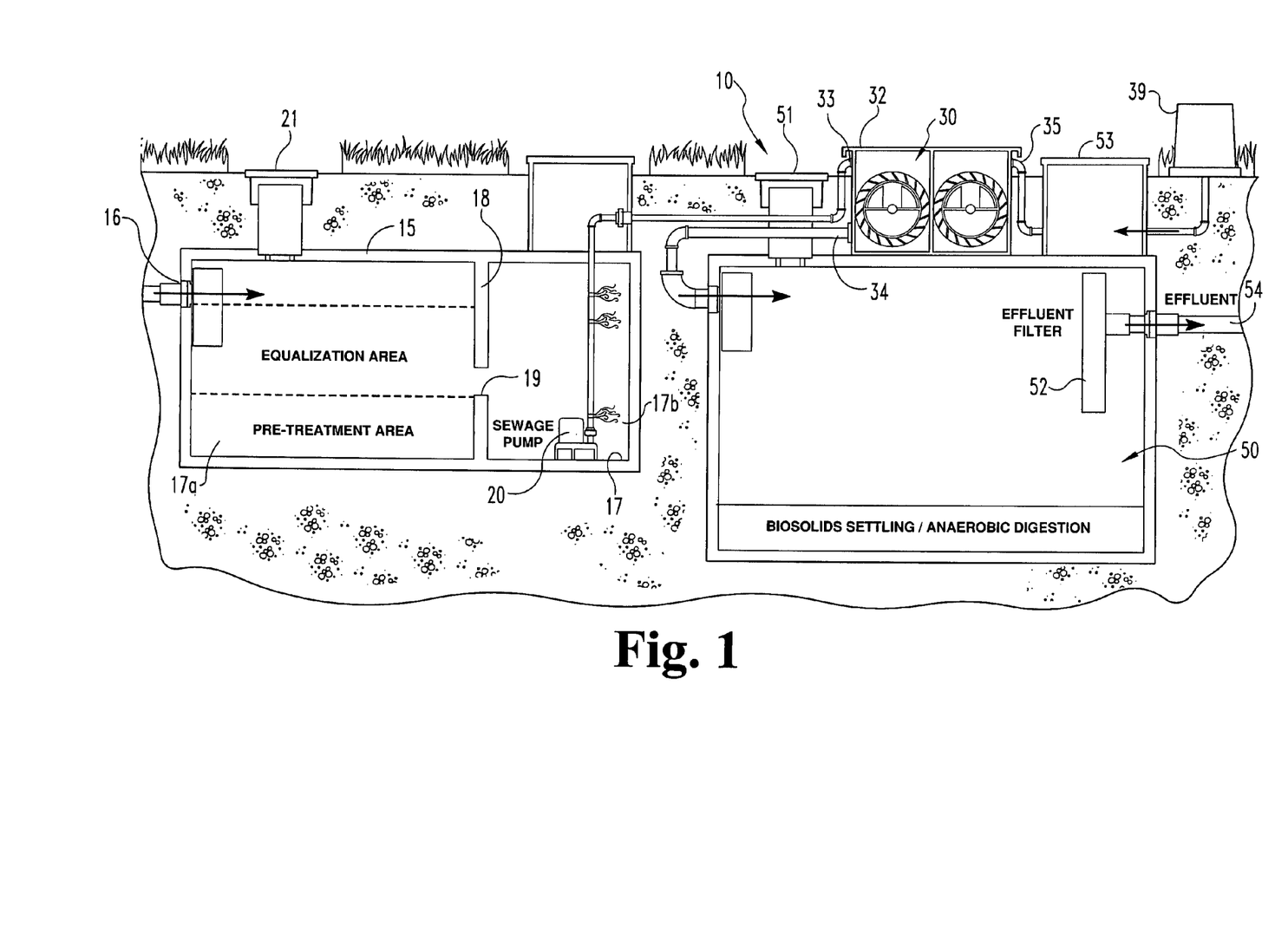
FIG. 1 is diagram of a wastewater treatment facility in accordance with one embodiment of the invention.

As shown in FIG. 1, the primary treatment tank 15 is buried underground. An access port 21 is provided that is accessible above ground for servicing the treatment tank 17. In particular, the access port 21 is adapted to receive equipment for removing the solids collected in the pre-treatment area at the bottom of the tank.

The outflow portion 17b is provided with a sewage pump that is adapted to pump wastewater from the primary treatment tank 15 to the secondary system 30. While the large inert solids will settle within the inflow portion 17a of the tank 17, the equalized wastewater will contain some amount of small solids. Thus, the pump 20 must be capable of pumping solid-laden water. The pump 20 may be controlled for timed operation and to provide metered flow to the secondary system 30. Alternatively, the pump may operate substantially continuously or may be activated when the equalized wastewater level within the tank 17 reaches a certain volume, such as in the nature of a sump pump. The mode of activation and operation of the pump 20 is linked to the operation of the secondary system 30.

Figure 2:
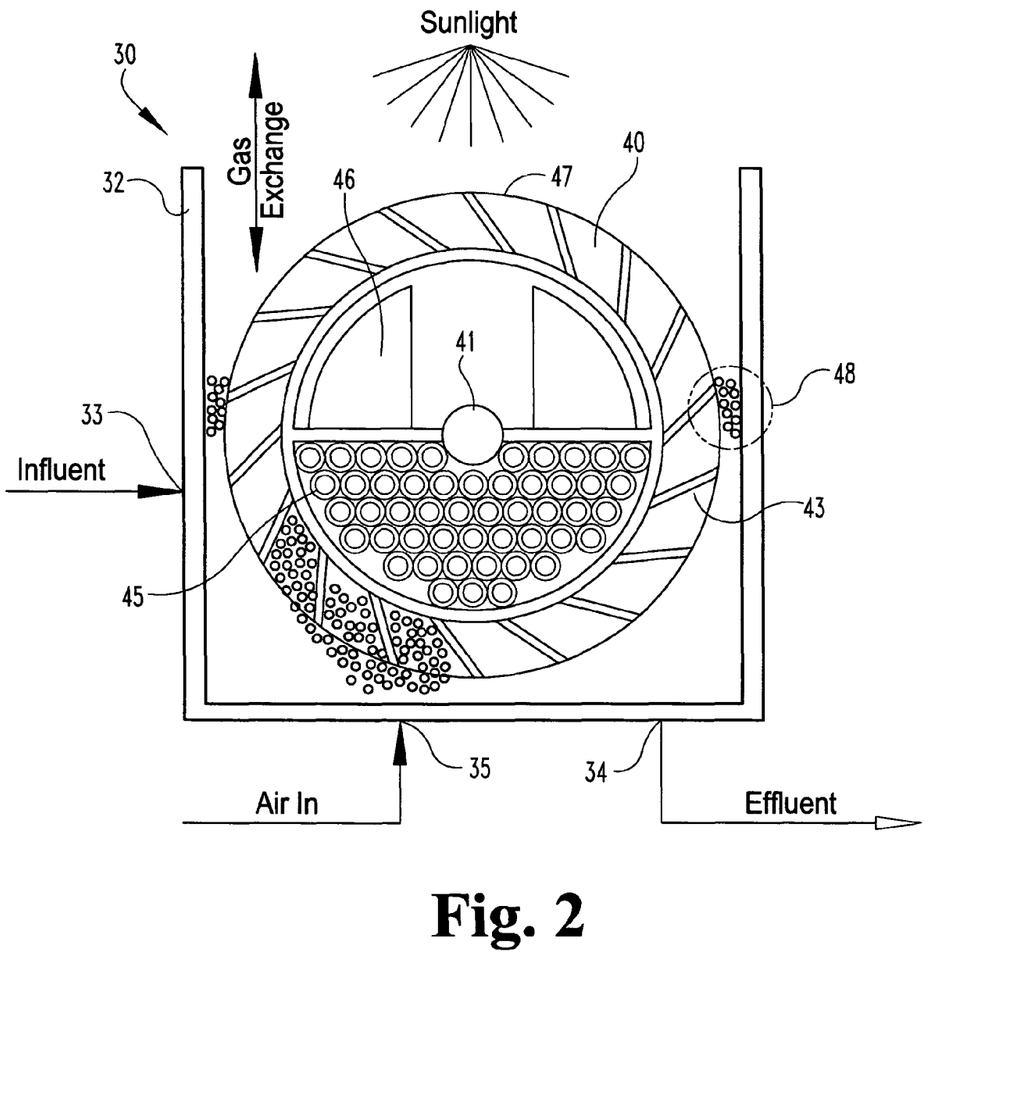
FIG. 2 is an enlarged diagram of a secondary treatment system used in the facility shown in FIG. 1.

The pre-treated wastewater is pumped into an inlet 33 in a tank 32 of the secondary treatment system 30. The secondary treatment system utilizes algae and bacteria to advantageously biologically treat the wastewater. The treated water is discharged from outlet 34 into the tertiary treatment tank 50, as shown in FIG. 1. In the preferred embodiments described herein, the secondary treatment system 30 employs technology described in U.S. Pat. Nos. 5,647,983, 5,755,961, and 6,158,386, the disclosure of which are all incorporated herein by reference, and particularly the disclosure of the treatment unit 45 as shown in FIG. 2 of those patents. While details of the treatment system 30 in the present treatment facility 10 may be obtained from these patents, a general description follows with reference to FIG. 2 of the present application.

It can be noted in FIG. 1 that the treatment system 30 is partially buried in the ground. The top face of the system must be above-ground for exposure to sunlight, as explained herein. However, the bulk of the system may be buried out of view, thereby improving the aesthetics of the facility 10.

A primary component of the secondary treatment system 30 is the media wheel 40 that is supported within the tank 32 for rotation about an axle 41. The media wheel 40 includes air capture members, or vanes, 43 that are used to rotate the wheel within the wastewater contained in the tank. In particular, a jet or flow of air provided by an external air pump 39 (FIG. 1) is directed through air inlet 35 to impinge on the vanes 43 to rotate the wheel. The vanes are preferably configured to, in effect, capture and air pocket between successive vanes so that the relative buoyancy of the air pocket will rotate the wheel as the air pocket rises within the tank. In addition to providing a motive force for rotating the media wheel, the air jet also introduces oxygen into the wastewater for beneficial reasons explained in more detail herein.

In the illustrated embodiment, the media wheel 40 includes a biological filter media 45 contained one portion of the wheel. This media is configured to support bacterial growth, such as polyethylene balls. As explained above, treatment of the wastewater requires the brining the biomaterials within the wastewater into contact with bacterial colonies that use the biomaterials as food. The wastewater level within the tank 32 is maintained so that the filter media 45 will be alternately submerged in and lifted out of the wastewater, which beneficially enhances the transfer of oxygen and $CO_2$ between the bacterial colony and the wastewater.

While one portion or half of the wheel interior is filled with the biological filter media 45, the remaining portion or half 46 is empty. Thus, as the media wheel 40 rotates, the filter media 45 alternately displaces the wastewater, producing a continuous movement or surge of the wastewater within the tank 32. This continuous movement increases the nutrient removal rate of algae carried by the wheel 40. More specifically, a screen 47 may be carried by the media wheel that is adapted to support algae growth. Movement of the screen 47 into and out of the wastewater provides for good gas exchange between the algae and the water and air, and provides a varying intensity of natural light on the algae, all of which leads to healthy and continuous growth of the algae.

The air jet at the inlet 35 is beneficial for the growth of the algae because the air jet foams and fractionates the wastewater. This foam 48 collects at the surface of the water between the media wheel 40 and the walls of the container. This foam bears against the screen 47 and more particularly the algae growing thereon so that the algae can readily extract the necessary nutrients from the entrained bio-solids within the foam.

It can be appreciated that the algae growing on the screen 47 forms a biomass that can be used for bio-diesel, fertilizer and other uses described above. The secondary treatment system 30 thus contemplates that the algae will be continuously dislodged from the screen 47 and allowed to pass into the tertiary treatment tank 50. The air jet through inlet 35 can dislodge algae from the screen once the algae colony reaches a critical mass. A scraper may also be provided, as described in U.S. Pat. No. 5,647,983 incorporated herein by reference. Once removed from the screen 47, the algae biomass settles to the bottom of the tank 32 where it can be withdrawn through outlet 34.

The outlet 34 communicates with the tertiary treatment tank 50, which is preferably buried beneath the secondary system 30, as shown in FIG. 1. As with the primary tank 15, the tertiary tank includes an access port 51 to provide access to the interior of the tank. It can be appreciated that one benefit of the facility 10 is achieved by the ability to bury the large primary and tertiary tanks underground. The tanks are not only hidden from, but also hidden from the elements. The only exposed part of the facility 10 is the secondary treatment system 30, which must be exposed to the atmosphere for gas exchange and to sunlight to facilitate algal bloom.

The tertiary tank 50 serves primarily as a settling tank for final removal of biosolids released from the secondary system 30, such as algae. The algae stripped from the screen 47 of the media wheel 40 produces a natural polymer which facilitates the settling of residual solids within the tertiary tank, as well as coagulation of the biomass, which facilitates removal. An effluent filter 52 is provided between the tank 50 and the effluence discharge outlet 54. A second access port 53 is provided to permit removal and cleaning of the filter 52. The outlet 54 may be discharged in a conventional manner, such as by subsurface disposal into a drainage field, or direct discharge into a stream or a municipal drainage system.

No additional treatment of the effluence is required (at least for normal biological residential or commercial wastewater) because the resulting effluent is free of the toxic materials present in the original wastewater. The total suspended solids (TSS) are also virtually eliminated through the primary and secondary elements of the facility. The nitrogen and phosphorous typically contained with wastewater is food for the bacteria and algae colonies resident within the secondary treatment system 30. The algae converts these toxic materials, through photosynthesis, into new compounds and oxygen. The oxygen oxidizes sewage solids, thereby facilitating compaction or coagulation of the solids. As explained above, the oxygen also fuels the growth of the bacterial colonies in the media wheel 40, while the bacteria produces $CO_2$ which helps fuel the growth of the algae. Thus, the facility 10 provides a virtually self-sustaining ecologically-driven cycle, fueled by the toxic materials in wastewater and sunlight. A typical facility 10 may be designed for an average daily flow of 10,000 gal/day, with a biological oxygen demand (BOD) of 500 ppm, a total suspended solids (TSS) of 250 ppm, an ammonia-nitrate composition of 30 ppm and a phosphorus content of 8 ppm. The effluent discharged from outlet 54 of the facility 10 contains less than 10 ppm BOD, less than 10 ppm TSS and less than 1 pm ammonia, which is well within environmental discharge limits. In some cases, post-processing may be required to meet all environmental guidelines. The outlet 54 may feed to a disinfection component (chlorine or ultraviolet light) or to an aeration component to increase the oxygen content of the effluent.

Figure 3:
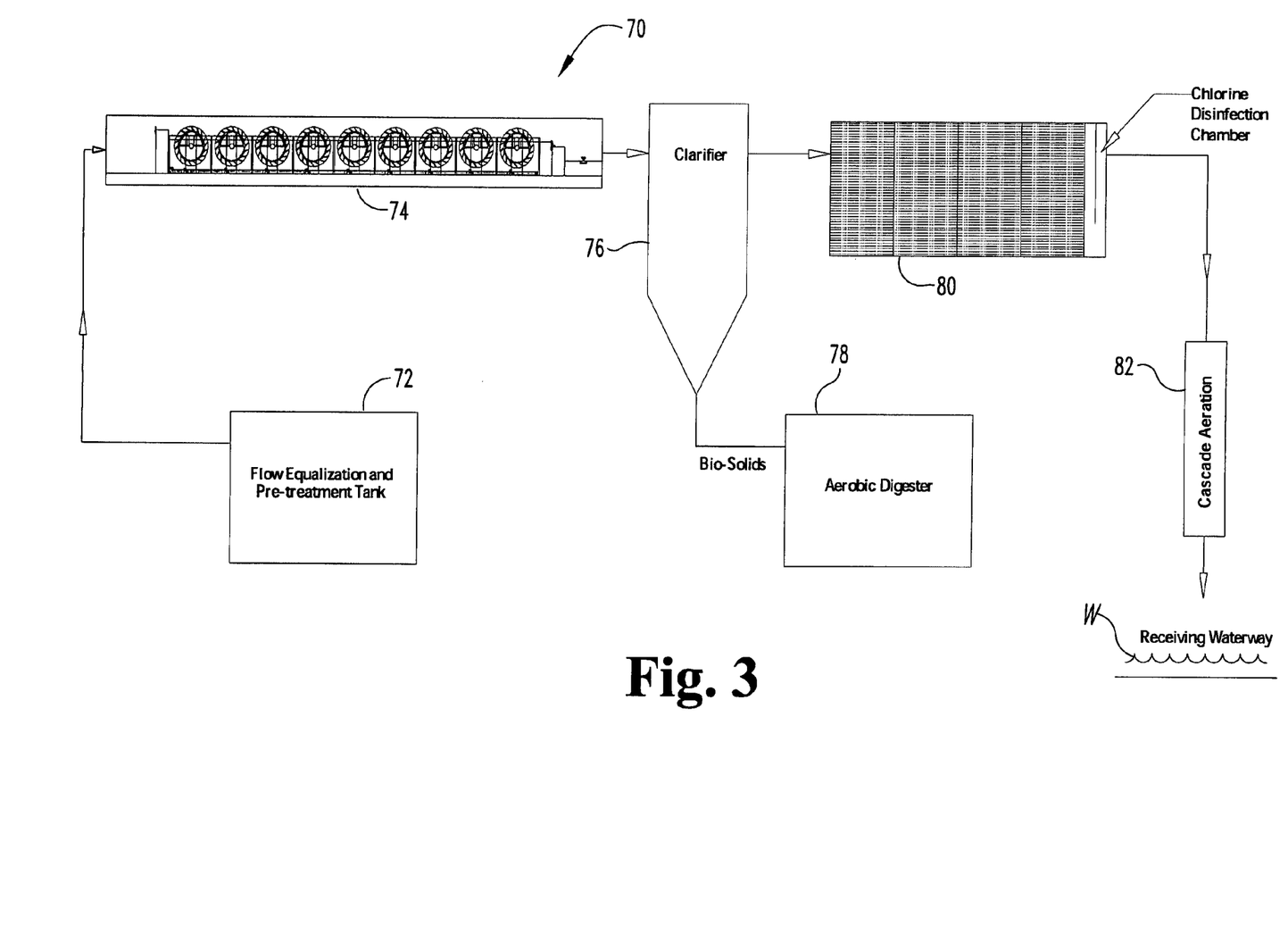
FIG. 3 is a diagram of an alternative wastewater treatment facility in accordance with the present invention.

Thus, one facility 70, depicted in FIG. 3, includes a primary treatment tank 72 and a secondary treatment system 74, each configured as described above. The discharge from the secondary treatment system is fed to a clarifier that extracts the biosolids for transport to an aerobic digester 78. The treated wastewater flows from the clarifier through a chlorine disinfection chamber 80 and a cascade aeration chamber 82 prior to discharge into a receiving waterway W.

One benefit of the facility 10 or 70 is that the biosolids resulting from the secondary treatment are efficiently collected within the tertiary tank 50 or 78. In some cases, the tertiary tank may provide anaerobic digestion of the biosolids, in some cases producing nitrogen gas that may be vented and collected. The biosolids may also be collected using known techniques, such as via a clarifier, centrifuge, mechanical press, belt filter press or other mechanical separation technology.

In the embodiment shown in FIG. 1, the secondary treatment system 30 is depicted with only two rotating media wheels 40. It is contemplated that the number of media wheels needed for the facility is determined by the flow rate of wastewater to be treated. As explained above, the facility 10 may be configured for a flow of only 500 gal/day, in which case the two media wheels shown in FIG. 1 may be appropriate. However, for larger flow systems, the greater volume of wastewater to be treated requires more bacterial and algal colonies, which thus requires more media wheels.

Figure 4:
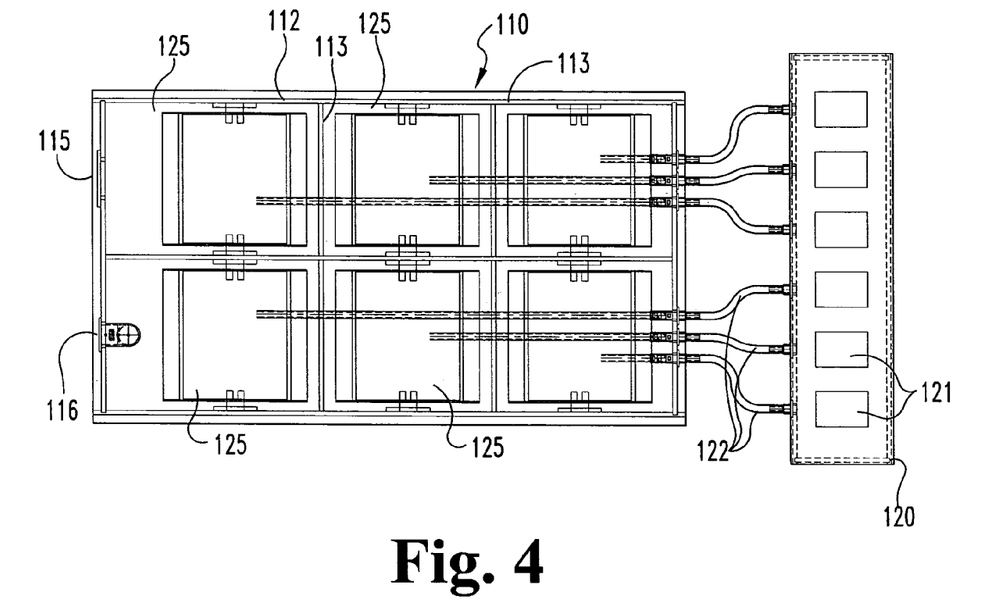
FIG. 4 is a top view of a secondary treatment system for higher wastewater flow rates.
Figure 5:
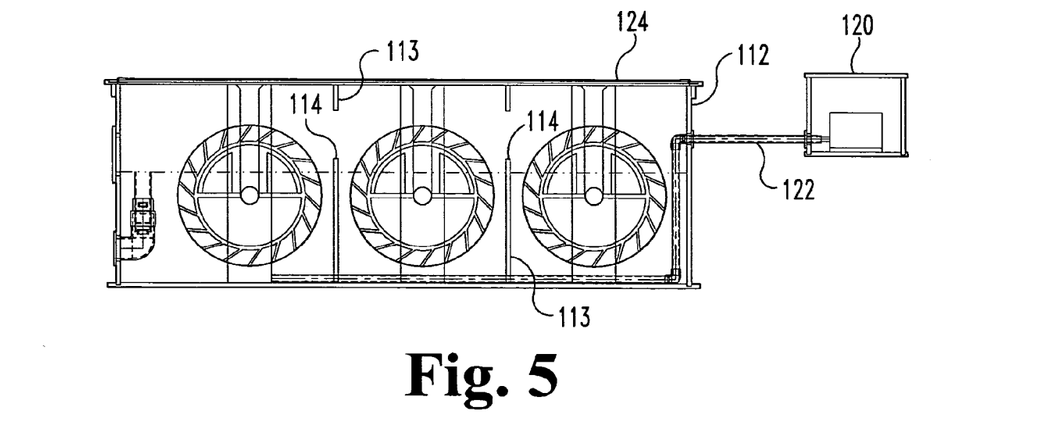
FIG. 5 is a side view of the secondary treatment system shown in FIG. 4.

Thus, in an alternative embodiment adapted for higher flow rates (such as up to 25,000 gal/day), the secondary treatment system may be the system 110 illustrated in FIGS. 4-5. Since the facility 10 is a continuous flow-through system it is not necessary for the primary and tertiary tanks to be larger than shown in FIG. 1. It is understood, however, that the piping that carries the effluent into inlet 16, to and from the secondary system 30, and out the outlet 54, must be sized appropriately.

In the embodiment shown in FIGS. 4-5, the secondary facility 110 includes a tank 112 that contains multiple media wheels 125—six in the specific illustrated embodiment. As shown in FIG. 5, walls 113 separate each media wheel 125, with a weir 114 defined in each wall to establish a common water level within the tank. Wastewater enters the tank 112 through inlet 115 and is discharged from outlet 116. In one specific embodiment, the outlet 116 includes a level control 117 that opens and closes the outlet 116 as needed to maintain the water level L at an optimum height within the container. In order to maintain optimum conditions for algae growth, it is desirable to control the amount of exposure of the algal colonies to the sunlight as the media wheels 125 rotate. If the water level L is too low, a greater portion of the circumference of the wheels is exposed to sunlight, and conversely if the water level is too high. In either case, too much or too little sunlight can compromise the desired conditions for optimum algae growth. Too little algae reduces the treatment capability of the system and reduces the biosolids produced by the system. The level control 117 may be a conventional float valve positioned at the opening of the outlet 116 within the container 112.

Since sunlight is critical to the function of the system 110, the container 112 is provided with a translucent or transparent lid 124. The lid keeps debris and wildlife from interfering with the operation of the system 110, while maintaining exposure of the media wheels to sunlight. The container 112 is preferably vented to reduce the greenhouse effect within the container.

The system 110 may include an array 120 of air pumps 121 that feed air to the media wheels through corresponding air tubes 122. Alternatively, a single air pump may supply air to a manifold from which each of the pipes 122 exit. However, in a specific embodiment, each media wheel 125 includes its own air pump 121. Each air pump may be capable of flow rates of about 1.25 cfm, although it is understood that the air flow rate (and ultimately the size of each air pump) is dictated by the desired rotational speed of the media wheels for optimum algae bloom.

Figure 6:
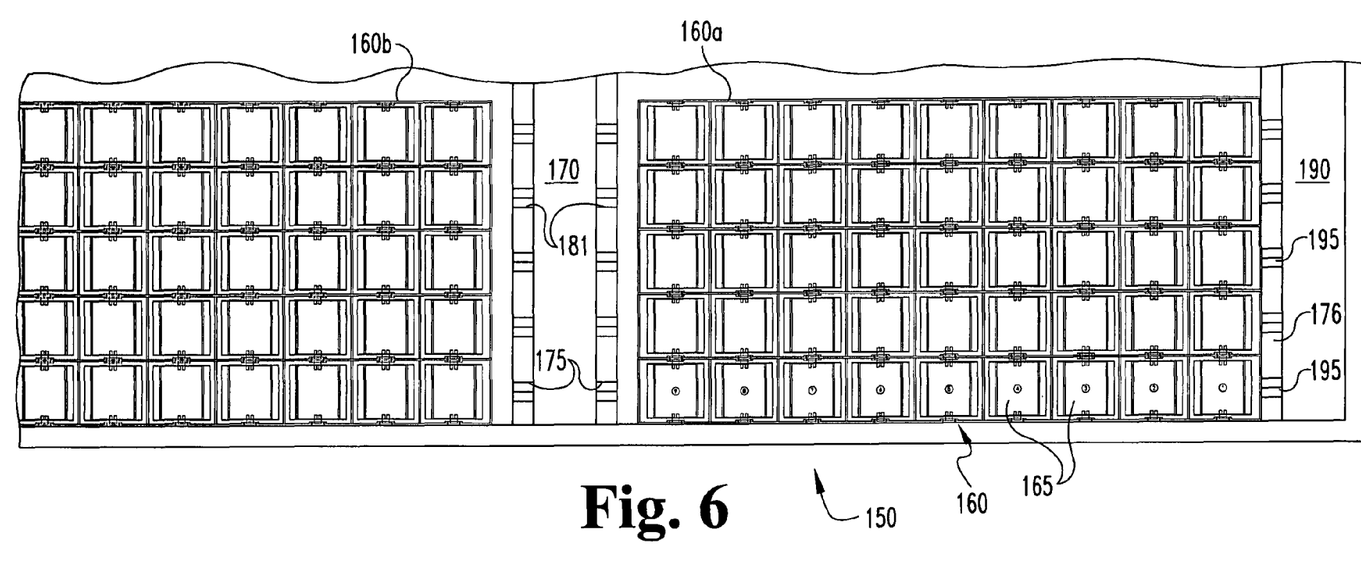
FIG. 6 is an enlarged partial top view of a wastewater treatment facility in accordance with another embodiment of the invention adapted for high volume wastewater flow rates.
Figure 7:
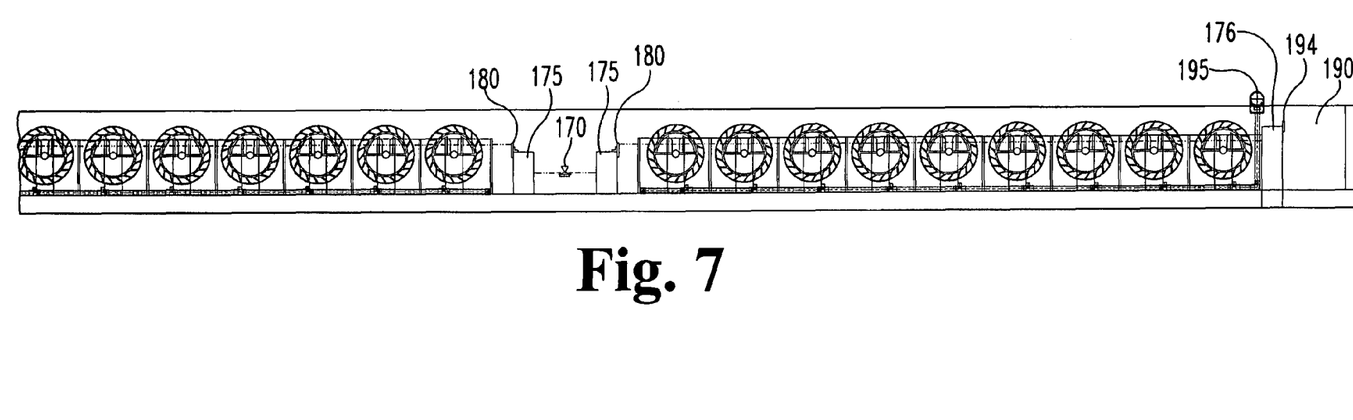
FIG. 7 is a side view of the facility shown in FIG. 6.
Figure 8:
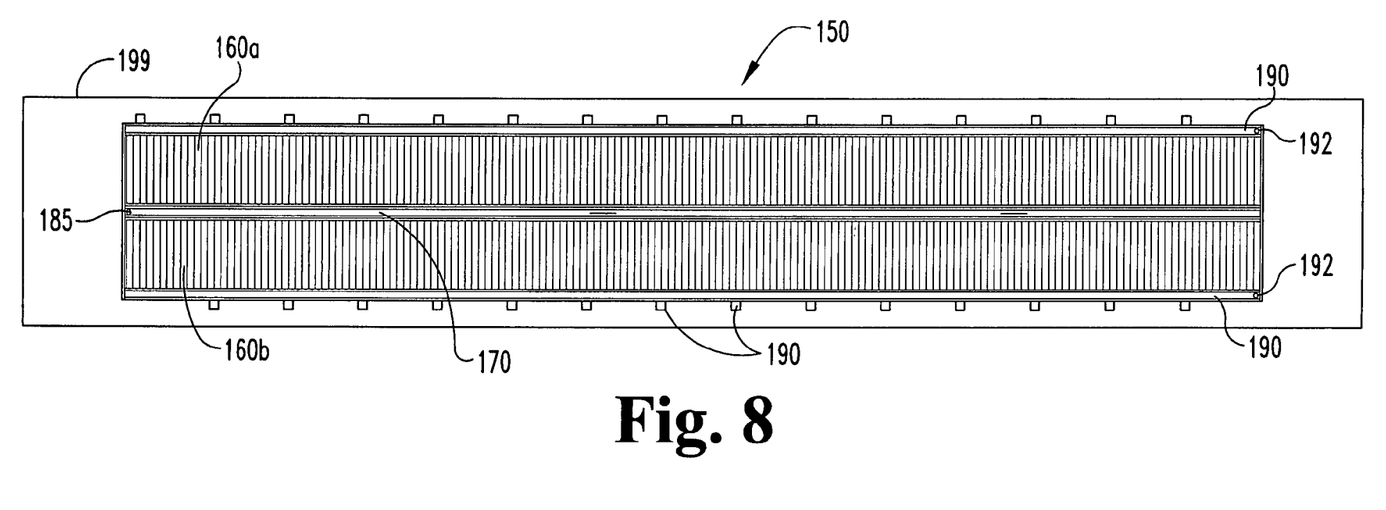
FIG. 8 is a top view of the entire facility of FIG. 6.

The present invention contemplates facilities of even larger scale to accommodate wastewater flow rates much greater than 25,000 gal/day. Two exemplary facilities are illustrated in FIGS. 6-8. The facility 150 includes a secondary treatment system 160 with many rotating media wheels 165. In one large scale system an array of 334 media wheels is provided, separated into two sections 160a, 160b. An effluent channel 170 separates the two sections 160a, 160b. The effluent channel 170 is defined by opposite walls 175, and the walls 175, along with outer side walls 176 define an enclosure or tank for the plurality of media wheels 165. A diverter plate 180 is carried by each effluent channel wall 175. The diverter plates define notches 181 at spaced intervals corresponding to each row of media wheels. The notches 181 thus provide controlled flow of the treated wastewater discharged from each row of media wheels into the effluent channel 170. As shown in FIG. 8, the effluent channel 170 feeds into a discharge pipe 185 that can carry the treated wastewater to tertiary treatment as described above.

The wastewater to be treated is supplied to the secondary treatment system 160 through inlet channels 190 feeding each section 160a, 160b of media wheels. Each inlet channel is connected to an intake pipe 192 that is connected to a source of wastewater. As with the effluent channel 170, the wall 176 includes a diverter plate 194 that includes notches 195 at spaced intervals corresponding to each row of media wheels. Thus, the notched diverter plate 194 operates to equalize the flow of wastewater into the secondary treatment system 160. The inlet channel 190 thus serves the function of the primary treatment tank 15 of the facility 10 in FIG. 1. However, the massive wastewater flow rates makes the use of sewage pumps problematic, so an open intake channel is preferable for this large scale facility 150.

As with the secondary treatment systems described above, the system 160 includes an air supply, which may be in the form of a conduit 195 connected to a source of pressurized air. A series of air blowers or pumps 196 are provided along the length of the conduit to maintain a proper air flow to each media wheel. In one specific embodiment in which the secondary treatment system 160 includes 167 media wheels per section 160a, 160b, fifteen air pumps 196 are provided with each section. Of course, the number of air pumps required for any particular facility depends upon the number of media wheels 165, which further depends upon the anticipated wastewater flow rate.

One benefit of the facility 150 is that the secondary treatment system 160 may be wholly contained within a greenhouse 199, as shown in FIG. 8. The greenhouse protects the treatment system 160, and particularly the media wheels 165, from debris and animals, while allowing sunlight to enter. The greenhouse is preferably vented with its own intake and discharge blowers to maintain an optimum atmosphere for operation of the media wheels. In the illustrated embodiment, the greenhouse 199 may be about 300 ft. long and 50 ft. wide. It is contemplated that this facility 150 can be constructed at a municipal waste treatment center or at an industrial complex. The land area occupied by the greenhouse 199 is significantly less than the area occupied by a typical wastewater treatment plant.

The facility 150 may form part of a larger system in which wastewater as well as waste $CO_2$ is treated and converted into other usable materials. First, with respect to waste $CO_2$, as explained above algae uses water, $CO_2$ and sunlight to grow. In the media wheels, the bacterial colonies supported by the filter media ingest the oxygen produced by the algae and emit $CO_2$ which is then used by the algae. For larger facilities, additional $CO_2$ may be beneficial to sustain a greater algae growth. Thus, $CO_2$ may be introduced into the greenhouse 199 of the facility 150, for instance, to augment or even replace the $CO_2$ generated by the bacterial colonies.

Figure 9:
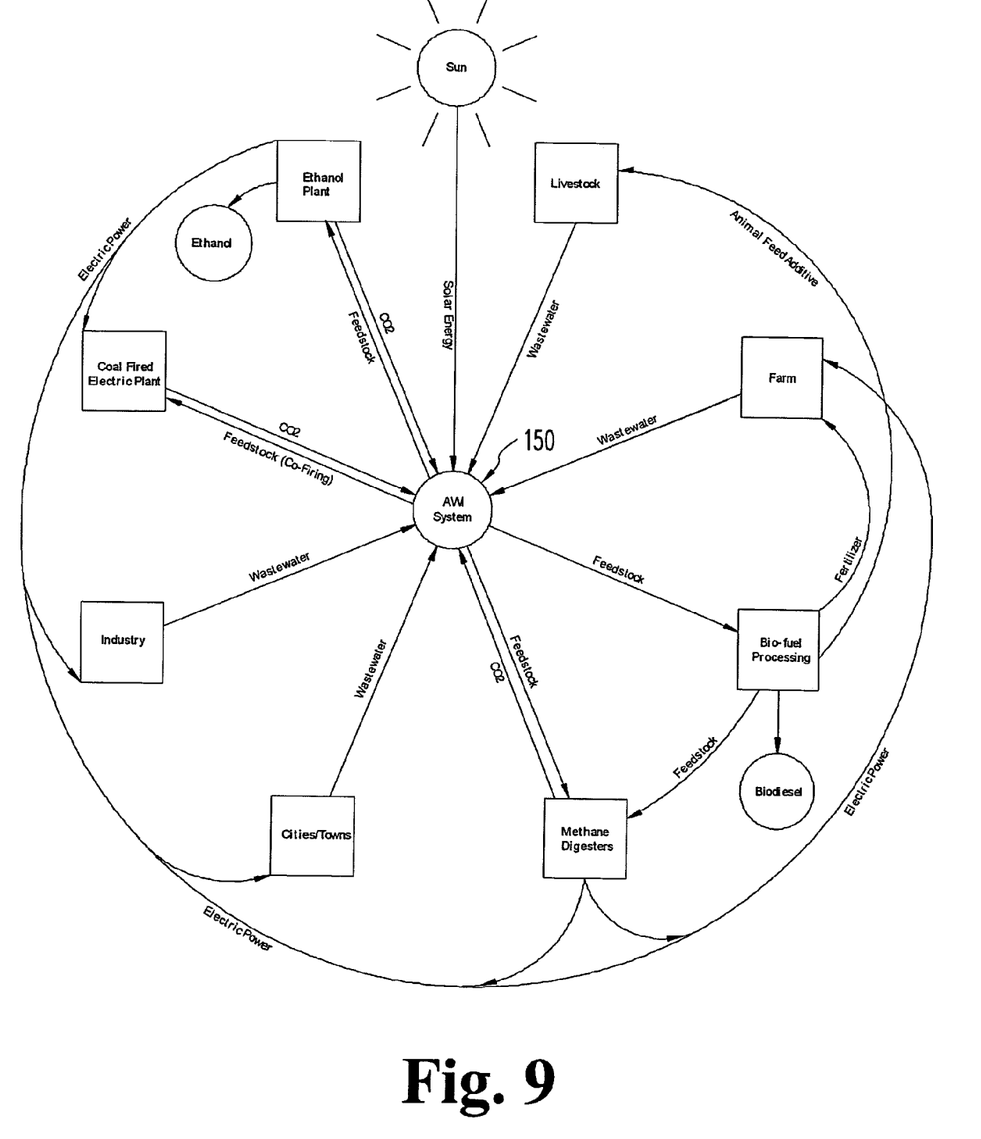
FIG. 9 is a process diagram of a globalized system using the wastewater treatment facilities of the present invention.

Consequently, a large scale or globalized system, such as the system depicted in FIG. 9, contemplates providing not only wastewater but also waste $CO_2$ to the treatment facility 150. A primary source of waste $CO_2$ is coal fired electricity generation plants, although ethanol production plants and methane digesters also produce $CO_2$ levels that exceed EPA limits for discharge into the atmosphere. Currently, this waste $CO_2$ must be treated in scrubbers, which necessarily adds initial and ongoing expense to producers of waste $CO_2$. In addition tote added expense, the scrubbed $CO_2$ is truly wasted, whereas with the present facility 150 the exhausted $CO_2$ can be collected and conveyed to the facility as food for the algae.

As expected, the facility 150 is especially provided for treating wastewater obtained by a wide range of sources, including industrial, municipal, agricultural and livestock. It should be understood that a particular treatment facility 150 may be associated with any one of these sources or where convenient may serve multiple sources of wastewater. For instance, an industrial park may incorporate a dedicated facility 150 that is distinct from a facility used for a nearby city. Of course, if the facility 150 is large enough it may receive wastewater from both the industrial park and the city. Similarly, wastewater from livestock may be treated separately or in combination with agricultural wastewater.

The secondary treatment systems disclosed herein may also be incorporated into a regenerative energy system in which the byproducts of the secondary treatment are used as fuel for electricity generation and the byproducts of the electricity generation are used as "fuel" for the secondary treatment. The entire regenerative energy system uses raw sewage as "fuel" and is essentially powered by solar energy so that the losses associated with the generated byproducts is minimal. Such a regenerative energy system 200 may be configured according to the process diagram shown in FIG. 10. Raw sewage is pumped by an existing pumping station 202 to a mechanical screen 205 that separates large solids that cannot be effectively treated in the secondary treatment facility 210a, and sends those large solids to biosolids storage 220. Algae biosolids from outside sources may also be collected in the biosolids storage.

Figure 10:
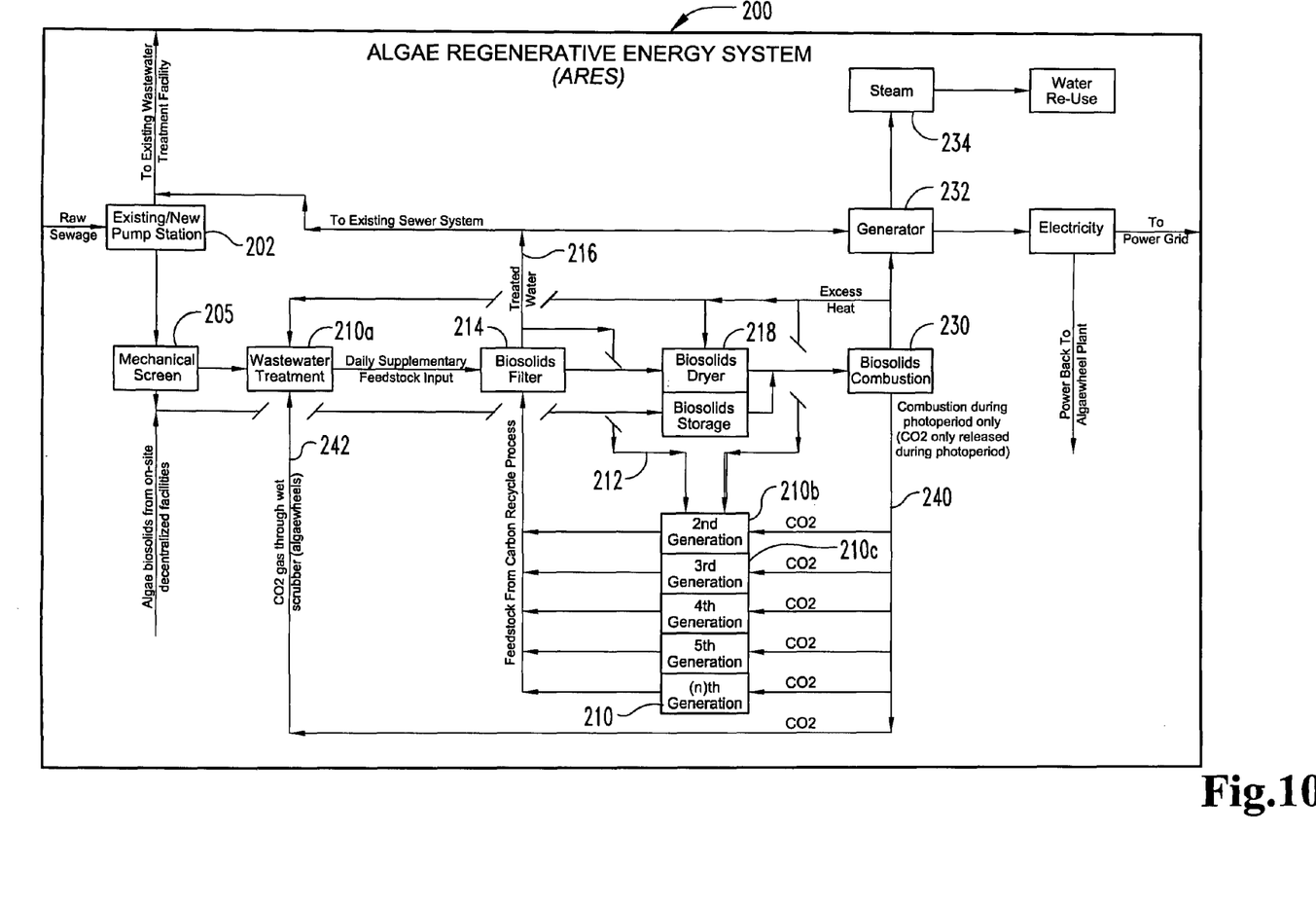
FIG. 10 is a process diagram of a regenerative energy system using the wastewater treatment facilities of the present invention.

The secondary treatment facility 210a may be constructed like the facility 150 described above. The treated biosolids generated by this facility are fed through a filter system 214 and introduced into a biosolids dryer 218. Once dried, the biosolids are sent to storage 220 for use in generating electricity. In particular, the biosolids are withdrawn from the storage 220 and combusted 230 to drive a generator 232. A portion of the treated water 216 produced by the treatment facility 214 that would otherwise be returned to the municipal sewer system may be provided to the generator 232 for conversion into steam by combustion of the biosolids. The output of the generator 232 is steam 234 that can be condensed into liquid water for re-use, and electricity that can be provided to the power grid. Some portion of the generated electricity is supplied to the electrical components of the treatment facility, such as motors, blowers and the like. In addition, some portion of the heat created during electricity generation may be diverted to the biosolids dryer 218 and to the secondary treatment facility 210a as needed.

The cycle of this process is completed by the transfer of exhaust gases 240 from the biosolids combustion 230 through a wet scrubber 242 back to the secondary treatment facility 210 to fuel the algae growth in the facility as explained above. The exhaust gases, namely $CO_2$, enhance and maximize algae production, which leads to increased biosolids production, which increases biosolids combustion 230, which results in greater electricity production. Although this cycle gives the appearance of a perpetual energy cycle, the external, and essentially limitless, power source for the entire process is solar energy.

The secondary treatment facility 210a is expected to treat the daily design flow for the specific raw sewage volume. Thus, it is contemplated that the facility 210a will be sized and configured to be solely dependent upon the nutrients contained in the wastewater provided at the pumping station 202. However, as suggested above, the regenerative aspects of the system 200 will produce greater amounts of combustion exhaust, namely $CO_2$, than is needed or that can be handled by the facility 210a. Rather than exhaust these gases to waste, the present invention contemplates bringing an additional treatment facility 210b on line. This additional facility would receive effluent 212 from the primary facility 210a as well as $CO_2$ and excess heat obtained from the electricity generation process. The algal growth cycle then commenced in this additional facility 210b until the same result is reached, namely that the algal growth has reached its limits in the additional facility and the byproducts have exceeded the capacity of the combination of the primary and additional facilities 210a, 210b. At that time, a third facility 210c may be brought on line. This sequence of events is repeated until the full complement of treatment facilities 210a-210(n) is reached, as determined by the desired output from the electricity generation processes. At that point, the exhaust gases that are not required to feed the many algae production facilities can be vented or stored in a suitable manner.

The treatment facilities 10, 70, 150 and 200 described herein provide a significant benefit in that the facilities are virtually self-sustaining, with the biological process being fueled by wastewater and sunlight. External power is required to operate the pump(s) drawing the wastewater from the source and to run the air pump(s) used to rotate the media wheels, add oxygen to the water and dislodge algae colonies for further processing. It is anticipated that any external power requirements for these facilities is significantly less than the power requirements for any prior treatment system for the waste water and waste $CO_2$.

In addition to the benefits of minimal external power requirements, the facilities described herein produce a byproduct from the biological processes occurring in the secondary treatment systems. With these facilities, new algae growth is continuous as long as new wastewater is supplied and sunlight is available. Thus, the secondary treatment systems are provided with means for periodically removing algae from the media wheels, with the security that new algae growth will occur in short order. The extracted algae can then be used as feedstock for outside processes. For instance, as illustrated in FIG. 9, the extracted algae can be provided to an ethanol plant for the production of ethanol fuel, to a coal-fired electric plant as an auxiliary fuel, to methane digesters for the production of methane, and to a processing plant for the production of fertilizer or bio-fuels, such as bio-diesel. Processes are known for using the algae in each of these environments, but to date the problem has been availability. In other words, there has been no renewable source of sufficient quantities of algae and bio-solids to support these external uses of the wastewater treatment by-products, or more pertinently to justify the investment in the processing facilities. The facilities 10, 70, 150 and 200 disclosed herein overcome these problems, especially for large scale facilities, such as the facilities 150 and 200 shown in FIGS. 6-8 and FIG. 10. The energy input to these facilities is primarily from the sun. The biological processes occurring in the secondary treatment systems are self-initiating and self-sustaining.

Moreover, the facilities disclosed herein perform their functions in a much reduced area than prior waste processing approaches. The ability to provide high volume waste treatment with limited land usage can make on-site treatment more readily available, thereby avoiding more costly or land intensive alternatives. For instance, in an industrial or municipal setting installation of a facility 70, 150 or 200 can eliminate the drainage and sewage pipe infrastructure traditionally necessary to transport wastewater to a distant treatment plant. On a smaller scale, such as for a farm, the smaller facility 10 of FIG. 1 can be used in lieu of a septic system, wastewater ponds or a traditional sewage infrastructure. The biomass byproducts from every facility, regardless of size, can be provided for any of the external uses identified in FIG. 9. Thus, the present invention provides an extremely environmentally-conscious solution to the ongoing problem of treating wastewater, with the beneficial adjunct of producing a renewable resource for use in other processes.

The wastewater treatment systems and processes of the present invention avoid the problems associated with prior biofuel production efforts. The rotating wheels of the secondary treatment systems (FIG. 2) essentially increase the available surface area for support algal growth. In the raceway ponds, the pond must be shallow enough for sunlight to reach the algae suspended and floating in the water flowing around the pond. With the present system, the rotating wheels continuously expose the algae colonies growing on the wheel surfaces to sunlight. Thus, the tank may be deep while the area occupied is minimized.

The prior raceway pond system requires injection of both $CO_2$ and nutrients into the pond for consumption by the algae. The system of the present invention utilizes both algae and bacteria which form a symbiotic relationship that leads to faster algal growth. While $CO_2$ may be introduced into the secondary treatment tank of the present inventive system, it is not necessary. However, additional $CO_2$ may support enhanced algae growth. Thus, the treatment system of the present invention may be used to treat both wastewater and waste $CO_2$ from an adjacent facility or factory.

Another benefit of the present system is that the algal biomass may be more easily extracted from the settling tank of this system than from the raceway pond of the prior system. The raceway pond requires the use of scrubbers or skimmers drawn through the pond or through a diverted flow in order the harvest the algae. On the other hand, the present inventive system relies upon the aeration jets used to rotate the wheels to dislodge the algal growth from the wheel surfaces. The dislodged algae will settle at the bottom of the stationary tank for easy removal. The biomass may be extracted from the tertiary treatment effluent by way of a centrifuge or belt filter press.

It has recently been discovered that algae produces significant amounts of hydrogen gas during its photosynthesis reactions. Thus, the facilities described above may be modified to extract hydrogen gas, which may then be used as a fuel. The prior raceway pond systems are not adapted for extraction of hydrogen since the hydrogen gas will percolate from the entire surface area of the pond. On the other hand, the secondary treatment system of the facility in FIG. 1 is contained and relatively small so that the hydrogen byproduct can be easily removed from each rotating wheel tank. The larger system 150 of FIGS. 6-8 is also readily adapted to extracting hydrogen gas emanating from an open media wheel systems 165, since the gas will collect at the top of the greenhouse 199.

The present invention contemplates integrating a wastewater treatment facility with systems for extracting and processing the biomass produced at the facility. The inventive system is entirely self-sufficient so long as biological wastewater is provided as influent. The small contained volume and the continuous movement of the water induced by the rotating wheels and the air injection insures that the water in the system will not freeze even in the harshest environments. The rotating wheel components optimize the surface area for supporting prolific algae growth, while also ensuring optimum exposure to sunlight. The compactness of the rotating wheel system means that a much greater amount of biomass may be produced in the same space ordinarily occupied by a raceway pond previously suggested for algae production.

The use of injected air to drive the rotating wheels significantly reduces the mechanical and electrical requirements for the system. Moreover, the manner and location at which the air is injected causes turbulence sufficient to dislodge an algae colony on a rotating wheel that has reached a critical mass. The present system further provides easy access for removing the biomass. In addition to the useful byproducts (biomass and hydrogen), the output of the inventive system includes clean water that may be reused at the adjacent facility. Thus, the present invention provides a threefold benefit—1) treatment of biological wastewater; 2) output of clean water that can be reused; and 3) output of biomass that can be used as a fuel, fertilizer or animal feed.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

For instance, while it is preferable for the media wheels to be rotated by air jets, as described above, other means for rotating the media wheels may be implemented. Where the secondary treatment system includes algae scrapers for scraping algae growth from the filter screen, the media wheels may be motor-driven since an air jet is not necessary to dislodge algae.

It is contemplated that the facilities described above may be used in a variety of climates under a wide range of sun conditions. As indicated above, it is contemplated that the continuous rotation of the media wheels within the secondary treatment system, together with the turbulence produced by the air jets directed into the wastewater will help prevent the wastewater within the secondary treatment tank from freezing. However, under extreme climate conditions an external heat source may be required to prevent freezing. In the facility 150, the greenhouse 199 will help avoid freezing due to the greenhouse effect, and at a minimum simplifies the use of an external heat source to maintain the wastewater above freezing. In the facility 10 shown in FIG. 1, the primary and tertiary tanks can be buried below the frost line to eliminate the risk of freezing.

Full scale operation of any of the facilities described above depends upon sunlight to fuel the photosynthesis processes of the algae colonies. As the amount of available sunlight decreases, so too does the water treatment and byproduct production capability of any of the facilities. In some cases, it may be desirable to augment the available sunlight with appropriate lamps, especially if the lamps can be powered by a renewable source, such as by wind power.

What is claimed is:

1. A process for wastewater treatment comprising:
   operating a first treatment facility operable to biologically treat wastewater to produce a substantially clean effluent and a byproduct of biosolids;
   using photosynthesis in the first treatment facility to increase the biosolids produced by the facility;
   extracting the biosolids from the first treatment facility;
   providing the biosolids to a separate facility for processing the biosolids; and
   recycling less than the entire output from the separate facility back to the first treatment facility to affect its operation.

2. The wastewater treatment process of claim 1, wherein the separate facility is a power generation plant operable to generate electricity from the combustion of the biosolids.

3. The wastewater treatment process of claim 2, wherein the recycled output of the power generation plant is $CO_2$.

4. The wastewater treatment process of claim 3, wherein the $CO_2$ output from the power generation plant is substantially completely attributable to combustion of the biosolids.

5. The wastewater treatment process of claim 4, wherein the recycled output includes excess heat from the combustion of the biosolids.

6. The wastewater treatment process of claim 2, wherein the recycled output of the power generation plant is electricity that is supplied to the treatment facility to power electrical components thereof.

7. The wastewater treatment process of claim 1, further comprising:
   operating one or more successive additional treatment facilities to receive effluent and recycled output from the separate facility when the capacity of the prior operated treatment facilities to use the recycled output is exceeded.

8. The wastewater treatment process of claim 7, wherein additional treatment facilities are added until a desired output of the separate facility is achieved.

9. The wastewater treatment process of claim 7, wherein the biosolids byproduct of each of the additional treatment facilities is combined and provided to the separate facility.

10. The wastewater treatment process of claim 1, wherein the step of providing the biosolids to a separate facility includes drying the biosolids extracted from the first treatment facility.

11. The wastewater treatment process of claim 10, wherein the recycled output includes excess heat from the combustion of the biosolids that is used to dry the biosolids.

12. The wastewater treatment process of claim 1, wherein the first treatment facility uses algae to increase the biosolids produced by the facility.

13. The wastewater treatment process of claim 1 further comprising removing biosolids from the wastewater prior to introduction to the first treatment facility and combining the removed biosolids with the biosolids extracted from the first treatment facility prior to being provided to the separate facility.

14. The wastewater treatment process of claim 1, wherein the separate treatment facility combusts the extracted biosolids.

15. The wastewater treatment process of claim 14, wherein at least a portion of the clean effluent is provided to the separate facility for conversion into steam.

* * * * *